US011690389B2

(12) United States Patent
Espin et al.

(10) Patent No.: US 11,690,389 B2
(45) Date of Patent: Jul. 4, 2023

(54) RED BEET PIGMENT COMPOSITION

(71) Applicants: CHR. HANSEN NATURAL COLORS A/S, Hoersholm (DK); UNIVERSITY OF COPENHAGEN, Copenhagen (DK)

(72) Inventors: Gregorio Barba Espin, Copenhagen (DK); Henrik Vik Luetken, Copenhagen (DK); Bjarne Joernsgaard, Hoersholm (DK); Renate Petra Brigitte Mueller, Copenhagen (DK); Tsaneta Dzhanfezova, Hoersholm (DK); Stephan Glied, Copenhagen (DK); Bjoern Madsen, Hoersholm (DK)

(73) Assignees: UNIVERSITY OF COPENHAGEN, Copenhagen (DK); OTERRA A/S, Hoersholm (DK)

( * ) Notice: Subject to any disclaimer, the term of this patent is extended or adjusted under 35 U.S.C. 154(b) by 498 days.

(21) Appl. No.: 16/649,173

(22) PCT Filed: Sep. 21, 2018

(86) PCT No.: PCT/EP2018/075607
§ 371 (c)(1),
(2) Date: Mar. 20, 2020

(87) PCT Pub. No.: WO2019/057896
PCT Pub. Date: Mar. 28, 2019

(65) Prior Publication Data
US 2020/0288757 A1 Sep. 17, 2020

(30) Foreign Application Priority Data
Sep. 22, 2017 (EP) .................................. 17192720

(51) Int. Cl.
*A23L 5/43* (2016.01)
*A23K 20/179* (2016.01)
*A01G 22/25* (2018.01)
*A61K 49/00* (2006.01)
*C09B 61/00* (2006.01)

(52) U.S. Cl.
CPC ................ *A23L 5/43* (2016.08); *A01G 22/25* (2018.02); *A23K 20/179* (2016.05); *A61K 49/006* (2013.01); *C09B 61/00* (2013.01); *A23V 2002/00* (2013.01)

(58) Field of Classification Search
None
See application file for complete search history.

(56) References Cited

U.S. PATENT DOCUMENTS 4,401,454 A  8/1983  Fritz et al.

OTHER PUBLICATIONS

Cao et al., "The effects of host defence elicitors on betacyanin accumulation in *Amaranthus mangostanus* seedlings," Food Chemistry, vol. 134, pp. 1715-1718 (Apr. 2012).
Chethana et al., "Aqueous two phase extraction for purification and concentration of betalains," J. Food Engineering, vol. 81, pp. 679-687 (Mar. 2007) (Available online Jan. 2007).
Goncalves et al., "A comparative study of the purification of betanin," Food Chemistry, vol. 131, pp. 231-238 (2012) (Available online Aug. 2011).
Bhandal et al., "Effect of Some Growth Substances and Phenolic Compounds on Membrane Permeability in Beet Root," Phyton Anneles rei Botanicae, pp. 177-184 (Feb. 1985).
Levy et al., "Effect of Ethylene-Releasing Compounds on Oleocellosis in 'Washington' Navel Oranges," Scientia Horticulturae, vol. 11, Issue 1, pp. 61-68 (Aug. 1979).
Reid, M.S., "New Aspects of the Practical Use of Ethylene-releasing Compounds," Plant Growth Substances, pp. 595-603 (1988).
Singh et al., "Effect of Plant Growth Regulators on Betacyanin Synthesis in *Celosia argentea* var.*cristata* in the dark," Z. Pflanzenphysiol. pp. 189-196 (Apr. 1976).

*Primary Examiner* — Susan Hoffman
(74) *Attorney, Agent, or Firm* — Jerold I. Schneider; Schneider IP Law

(57) ABSTRACT

A method for obtaining a betalain pigment composition from red beet plants comprising pre-harvest foliar spraying of an ethylene-generating compound and the use of the obtained betalain pigment composition for coloring of an edible product.

12 Claims, No Drawings

RED BEET PIGMENT COMPOSITION

CROSS-REFERENCE TO RELATED APPLICATIONS

This application is the U.S. National Stage of International Application PCT/EP2018/075607, filed Sep. 21, 2018, and claims priority to European Patent Application No. 17192720.5, filed Sep. 22, 2017.

FIELD OF THE INVENTION

The present invention relates to a method for obtaining a betalain pigment composition from red beet plants comprising pre-harvest foliar spraying of an ethylene-generating compound, the obtained betalain pigment composition and the use of the obtained betalain pigment composition for coloring of an edible product.

BACKGROUND ART

There is increasing demand for natural food colorants that can substitute synthetic colors due to both aggravated legal restrictions and consumer concerns. Red beets (*Beta vulgaris* L. spp. *vulgaris*) known as beetroot, are a source of natural colorant betalains. Betalains are wide-spread water-soluble pigments which substitute anthocyanins in plants within the Caryophyllales order. Betalains have higher water solubility and tinctorial strength than anthocyanins. Betalains represent excellent replacements for artificial red-purple food colors.

Betalains are well known as a group of compounds giving color to food, vegetables and flowers and are responsible for the red, orange and yellow color of many plant species. Betalains are non-toxic pigments and therefore betalains extracted from fruit and vegetables have been used as food colorants for providing colors in the red to yellow color range.

The betalain composition obtainable from red beet comprises two different water-soluble groups of pigments namely red-purple betacyanidins and yellow betaxanthins. In mature beetroots, 75-90% of total betacyanidins consist of the pigment betanin which is red. Betaxanthins account for a minor part of the betalain composition, where vulgaxanthin, which is yellow, is the most dominant of betaxanthins present.

There is a constant desire to improve the pigment composition obtained from red beet; improved stability, higher yield, brighter colors, etc.

Compounds that generate ethylene when sprayed on plants have become of major economic importance, being used to accelerate diverse ethylene responses such as induction of flowering, stimulation of latex flow, leaf and branchlet abscission, fruit ripening, fruit abscission, and pod dehiscence.

A number of such ethylene-generating compounds are known in the art—suitable examples are e.g. Ethephon, Silaid, Alsol, ACC (M. S. Reid, 1988; Yoseph Levy et al. 1979).

Chethana et al: "Aqueous two phase extraction for purification and concentration of betalains", J. Food Eng., vol. 81, no. 4, 15 Mar. 2007, p. 679-687 disclose purified betalain pigment compositions obtained by extraction of beetroots. The two phase extraction resulted in removal of sugars and polymers resulting in a purified betalain composition.

Leticia Christina Pires Gonalves et al: "A comparative study of the purification of betanin", Food chemistry, vol. 131, no. 1, 23 Aug. 2011, p. 231-238 also disclose purified betalain pigment compositions obtained by seven different methods, ion exchange chromatography being the most efficient method. The purified samples comprised a higher amount of its epimer isobetanin than fresh extract.

U.S. Pat. No. 4,401,454, Fritz Charles et al, 30 Aug. 1983 relates to a growth regulation process to obtain crop yield. Increase in color of the crop is not identified or focused on, further no root plants were investigated and for potatoes which are also under ground the application of the compounds was applied to the potato before planting and not sprayed onto the leaves.

Singh O. S. et al: "Effect of plant growth regulators on beta cyanin synthesis in *Celosia-argentea* var. *christata* in the dark", Z. Planzenphysiol. April 1976, p. 189-196 describes germinated seeds of *Celosia argentea* var. *christata* incubated in petri dishes comprising either auxin, cytokinin, an inhibitor or ethylene to investigate their effect on betacyanin synthesis on seedlings grown under dark conditions.

In Shifeng Cao et al: "The effects of host defence elicitors on betacyanin accumulation in seedlings", Food Chemistry, 5 Apr. 2012, vol. 134, no. 4, p. 1715.1718, seeds of *A. Mangostanus* were germinated in buffer comprising Ethephon. The Ethephon treatment of seedlings showed that 0.1 mM and 1 mM did not elicit pigment accumulation in the Ammaranthus seedlings whereas 5 mM seemed to have an effect.

In Iqbal Singh Bhandal et al: "Effect of some growth substances and phenolic compounds on membrane permeability in Beet Root", Phyton. Annales Rei Botanicae, vol. 25, no. 1, 28 Feb. 1985, p. 177-184, beet root was used as an experimental material in the investigation where betacyanin efflux and conductivity changes were taken as the two parameters of permeability. It showed that Ethephon promoted beta cyanin efflux at 50 ppm.

Testing of Ethephon spraying of beet root plants (on the leaves) and the investigation of the effect on pigment accumulation on another plant organ than the treated during growth has never been seen before.

SUMMARY OF THE INVENTION

The present invention relates to a method for increasing the concentration of betalains and the betanin to vulgaxanthin ratio in red beets.

It has surprisingly been found that by pre-harvest spraying of an ethylene-generating compound on red beet leaves the mean betalain pigment concentration in the roots of the treated red beet plants increased significantly when compared with their respective controls. It has also surprisingly been found that the pre-harvest foliar spraying of red beet plants increases the betanin to vulgaxanthin ratio in the betalain composition of red beet. It has further surprisingly been found that the pre-harvest foliar spraying of red beet plants increases the betalain to total soluble solids ratio in the red beet.

A first aspect of the present invention relates to a method for obtaining a betalain pigment composition from red beet plants comprising the following steps:
(i): foliar spraying red beet plants with an ethylene-generating compound;
(ii): harvesting the red beet plants sprayed in step (i); and
(iii): isolating betalains from the red beet plants harvested in step (ii) and thereby obtain a betalain pigment composition.

A second aspect of the present invention relates to a betalain pigment composition obtained according to the method of the first aspect and/or an embodiment thereof.

A third aspect of the present invention relates to the use of a betalain pigment composition obtained according to the method of the first aspect and/or an embodiment thereof for coloring of an edible product.

DETAILED DESCRIPTION OF THE INVENTION

The betalain pigment composition obtainable from red beet comprises two different groups of water-soluble pigments namely the red-purple betacyanidins and the yellow betaxanthins. In mature beetroots, 75-90% of total betacyanidins consist of the pigment betanin, which is red. Betaxanthins account for a minor part of the betalain composition, where vulgaxanthin, which is yellow, is the most dominant. Betanin is more stable than vulgaxanthin both at room temperature and upon heating.

For the above mentioned reasons it is a desire to increase the betanin to vulgaxanthin ratio in the red beet pigment composition to obtain a more bright red color.

The present invention relates thus to a method for obtaining a betalain pigment composition from red beet, which gives an increased yield of betalains in particular betanins and/or a higher ratio of betanin to vulgaxanthin.

A particular embodiment of the present invention relates to a method for obtaining a betalain pigment composition from red beet plants comprising the following steps:
  (i): foliar spraying red beet plants with an ethylene-generating compound;
  (ii): harvesting the red beet plants sprayed in step (i); and
  (iii): isolating betalains from the red beet plants harvested in step (ii) and thereby obtaining the betalain pigment composition.

It is evident that the red beet plants are herein red beet plants that are capable of producing betanin pigments.

In a preferred embodiment the red beet is a *Beta vulgaris* L. spp. *vulgaris*.

The term "foliar spraying" relates to a technique of spraying plants by applying liquid active ingredients directly onto their leaves. In the present invention the foliar spaying involves application of one or more ethylene-generating compounds directly to the leaves of the red beet plant.

The term "ethylene-generating compound" in the following also referred to as "egc" relates herein to a compound that release ethylene when sprayed on plants or act as an ethylene precursor like ACC (1-aminocyclopropane-1-carboxylic acid).

Ethylene generating compounds relevant for the present invention include but are not limited to (2-chloroethyl) phosphonic acid, (2-chloroethyl)methylbis(phenylmethoxy)-silane, (2-chloroethyl)tris(2-methoxyethoxy)silane and/or 1-aminocyclopropane-1-carboxylic acid. The ethylene-generating compound of the present invention is also referred to as the active ingredient.

A number of such ethylene-generating compounds are commercially available e.g. 2-chloroethylphosphonic acid under the tradenames Ethephon, Bromeflor, Arvest and Ethrel, 2-chloroethylmethylbis(phenylmethoxy)silane or bis(benzyloxy)(2-chlomethyl)-methylsilane under the tradename Silaid, and 2-chloroethyltris(2-methoxyethoxy)silane under the tradename Alsol.

In a particular embodiment of the present invention two or more different ethylene-generating compounds are used.

In a preferred embodiment of the present invention the ethylene-generating compound is 2-chloroethylphosphonic acid.

The method of the present invention may preferably be used for commercially relevant large scale production of betalain pigments, i.e. large scale isolation from red beet plants.

Accordingly, it may be preferred that the isolation of betalains in step (iii) is done from at least 15 different harvested red beet plants which have been foliar sprayed with an ethylene realizing compound, more preferably from at least 100 different harvested red beet plants, even more preferably from at least 500 different harvested red beet plants, such as from at least 1000 different harvested red beet plants.

In a particular embodiment of the present invention the amount of betalain pigments in the sprayed beetroots and/or betalain pigments obtained in step (iii) of the method of the first aspect is an amount of betalain pigment which is at least 4% (w/w) higher, more preferably at least 5% (w/w) higher, even more preferably at least 7% (w/w) higher and even more preferably at least 8% (w/w) higher such as 10% (w/w) higher and even 15% (w/w) higher as compared to the amount of betalain pigment that is obtained in a control experiment without use of ethylene-generating compound in step (i).

The amount of betalain pigment in the beetroots is given as the total amount of betanin and vulgaxanthin.

The amount of betanin pigment in the red beet plants is measured according to the following method: The washed beetroots are ground and homogenized in a 3% sulfuric acid solution (1/1, w/w). The resulting fine homogenate is subsequently mixed with demineralized water (1/2, w/w), vortexed and centrifuged for 20 min at 4500 rpm, the resulting supernatant is diluted to a proper concentration, for the spectrophotometer used, in 33 mM $KH_2PO_4$ (pH 6.5), and the absorbance is measured at 476 nm for betanin, using a UV-visible spectrophotometer.

The absorbance obtained is then used to calculate the betanin concentration using the formula: betanin concentration of red beet=$A \times DF \times MW / \varepsilon \times L$ [mg kg$^{-1}$]; where A is the absorption value of the diluted betanin corrected for absorbance of vulgaxanthin at 476 nm, DF is the dilution factor, from redbeet to the measured sample, MW is the betanin molecular weight, $\varepsilon$ is the molar extinction coefficient and L is the path length of the cuvette.

The amount of vulgaxanthin pigment in the red beet plants is measured according to the following method: The washed beetroots are ground and homogenized in a 3% sulfuric acid solution (1/1, w/w). The resulting fine homogenate is subsequently mixed with demineralized water (1/2, w/w), vortexed and centrifuged for 20 min at 4500 rpm, the resulting supernatant is diluted to a proper concentration, for the spectrophotometer used, in 33 mM $KH_2PO_4$ (pH 6.5), and the absorbance is measured at 538 nm for vulgaxanthin, using a UV-visible spectrophotometer.

The absorbance obtained is then used to calculate the vulgaxanthin concentration using the formula: vulgaxanthin concentration of red beet=$A \times DF \times MW / \varepsilon \times L$ [mg kg$^{-1}$]; where A is the absorption value of the diluted vulgaxanthin corrected for absorbance of betanin at 538 nm, DF is the dilution factor, from redbeet to the measured sample, MW is the betanin molecular weight, $\varepsilon$ is the molar extinction coefficient and L is the path length of the cuvette.

In a particular embodiment of the present invention the amount of betanin pigments in the sprayed beetroots and/or betanin pigments obtained in step (iii) of the method of the first aspect is an amount of betanin pigment which is at least 5% higher (w/w), such as at least 7% higher (w/w), such as at least 10% higher (w/w), such as at least 12% higher (w/w), such as at least 15% higher (w/w), such as at least 20% higher as compared to the amount of betanin pigment that is obtained in a control experiment without use of ethylene-generating compound in step (i).

In a particular embodiment of the present invention the betanin to vulgaxanthin ratio is at least 5:1, in a more particular embodiment the betanin to vulgaxanthin ratio is at least 5.5:1, in a most particular embodiment of the present invention the betanin to vulgaxanthin ratio is at least 6:1. In a further embodiment of the present invention the betanin to vulgaxanthin ratio is less than 20:1, such as less than 15:1.

In a further embodiment of the present invention the betanin to vulgaxanthin ratio has increased by at least 5%, such as at least 10%, such as at least 15%, such as at least 20% compared to the control sample not being foliar sprayed with an ethylene generating compound.

In a particular embodiment of the present invention the betalain to TSS (Total Soluble solids) ratio has increased by at least 5%, such as at least 10%, such as at least 15%, such as at least 20% compared to the control sample not being foliar sprayed with an ethylene generating compound.

The TSS is measured with a manual refractometer (Refracto 30PX/GS Mettler-Toledo Inc., OH, USA) operating in the 0% to 85% Brix range. The beetroot extract is filtered through 0.45 μm membrane filters, and Brix measurements are performed using 1 mL of the filtrate.

As understood by the skilled person in the present context, the purpose of a control experiment is to analyze the effect of using an ethylene-generating compound. Accordingly, everything in the control experiment (e.g. harvesting time in step (ii), specific method of isolation in step (iii), etc.) shall be identical to the method using the ethylene-generating compound of the first aspect.

In a particular embodiment of the present invention the total amount of ethylene-generating compound applied by spraying in step (i) on the red beet crop from sowing to harvest is an amount of more than 50 g egc ha$^{-1}$ to 10000 g egc ha$^{-1}$ Preferably, the amount of ethylene-generating compound applied in step (i) is an amount of from 100 g egc ha$^{-1}$ to 5000 g egc ha$^{-1}$, more preferably it is an amount of from 200 g egc ha$^{-1}$ to 2500 g egc ha$^{-1}$, such as e.g. an amount of from 400 g egc ha$^{-1}$ to 1250 g egc ha$^{-1}$; such as e.g. an amount of from 400 g egc ha$^{-1}$ to 1250 g egc ha$^{-1}$.

In a particular embodiment of the present invention the amount of ethylene-generating compound applied at each spraying in step (i) is an amount of from 20 g egc ha$^{-1}$ to 5000 g egc ha$^{-1}$. Preferably, the amount of ethylene-generating compound applied in step (i) is an amount of from 100 g egc ha$^{-1}$ to 1000 g egc ha$^{-1}$, more preferably it is an amount of from 200 g egc ha$^{-1}$ to 500 g egc ha$^{-1}$.

In a particular embodiment of the present invention the amount of ethylene-generating compound applied at each spraying in step (i) is more than 20 g egc ha$^{-1}$ such as more than 50 g egc ha$^{-1}$, such as more than 100 g egc ha$^{-1}$, such as more 200 g egc ha$^{-1}$ The amount of ethylene-generating compound applied at each spraying in step (i) is particularly less than 5000 g egc ha$^{-1}$, such as less than 1000 g egc ha$^{-1}$, such as less than 500 g ha$^{-1}$.

In a particular embodiment of the present invention the foliar spraying of ethylene-generating compound is done later than 1 week after planting, preferably it is done later than 2 weeks after planting. It may be preferred that it is done later than 4 weeks after planting.

It may be preferred that the foliar spraying of the ethylene-generating compound of step (i) is done more than one time (such as e.g. 2 times) before the harvesting the red beet plants of step (ii). It may be preferred that it is done at least 3 times before harvesting the red beet plants of step (ii), such as at least 4 times, such as at least 5 times before harvesting the red beet plants, or even 6 times or more before harvesting.

Step (ii) of the first aspect relates to harvesting the red beet plants of step (i). Harvesting done in step (ii) is done as known in the art.

In relation to step (ii), it may be preferred that harvesting of the red beet plants of step (ii) of the first aspect is done later than 4 weeks after planting, preferably it is done later than 6 weeks after planting, such as later than 8 weeks after planting. In a further embodiment the harvesting of the red beet plant of step (ii) is done before 25 weeks after planting, such as before 20 weeks after planting. In a particular embodiment the harvesting is between 8 to 15 weeks, such as 10 to 14 weeks.

Step (iii) of the first aspect relates to isolating betalains from the harvested red beet plants of step (ii) and thereby obtain the betalain pigment composition. Thus, the betalains are extracted from the beetroots.

The term "isolating" in step (iii) should be understood as some liquid (e.g. water) and/or solids are separated from the betalains—i.e. the betalain pigment composition does not comprise all liquid (e.g. water) and/or solids of the red beets.

In a particular embodiment of the present invention the isolation of betalains from the beetroots are performed by washing the beetroots and splitting them lengthwise. The beetroots are ground and homogenized in a 3% sulfuric acid solution (1/1, w/w). The resulting fine homogenate is subsequently mixed with demineralized water (1/2, w/w) and vortexed. Finally, the sample is centrifuged for 20 min at 4500 rpm.

For instance, the in step (iii) obtained betalain pigment composition may be a juice.

The skilled person routinely knows how to perform step (iii)—i.e. it may be done according to the art, such as by extraction from the roots of the harvested red beet plants.

The isolating of the betalains of step (iii) may include but are not limited to any of the following steps; extraction of the betalain pigments by washing the raw beets, breaking, grinding, heating, adding enzymes and water, stabulation, decantation, pressing, resin-purification and concentration by water or other liquid removal, drying e.g. spray and/or freeze drying.

The betalain pigment composition of the present invention may be in liquid or powder form. It may have a purity which is higher than 0.3% of betalain in liquid form or more than 0.5% in powder form. Purification may be performed e.g. by purifying with macroporous resins to obtain a desired degree of purity. Purification may be performed e.g. by use of High Performance Liquid Chromatography (HPLC) to obtain a desired degree of purity.

The pigment composition of the present invention may be a liquid composition or a powder composition. In a particular embodiment the composition of (iii) is dried. Preferably the composition is dried in a spray drier. In a particular embodiment the composition comprises less than 10% water, such as less than 5% water.

It may be preferred that the in step (iii) obtained betalain pigment composition is a liquid composition or a dried composition that comprises less than 60% (w/w) of liquid (e.g. water) such as less than 50% (w/w), such as less than 40% (w/w), such than less than 30% (w/w).

The present invention further relates to the use of the betalain pigment composition obtained according to the method of the present invention for coloring of an edible product.

The edible product of the present invention includes a food product, a feed product, a pharmaceutical and/or therapeutic product for oral administration.

The food products of the present invention include but are not limited to dairy products, juice, beverage, wine gum, marmalade, jam, confectionary, panned chocolate lentils, sausage casings, pasta, macaroni, cheese, prepared foods and/or extruded foods.

The following items are preferred embodiments of the present invention:

Item 1. A method for obtaining a betalain pigment composition from red beet plants comprising the following steps:
  (i): foliar spraying red beet plants with an ethylene-generating compound;
  (ii): harvesting the red beet plants sprayed in step (i); and
  (iii): isolating betalains from the red beet plants harvested in step (ii) and thereby obtaining the betalain pigment composition.

Item 2. A method for obtaining a betalain pigment composition from red beet plants comprising the following steps:
  (i): foliar spraying red beet plants with an ethylene-generating compound;
  (ii): harvesting the red beet plants sprayed in step (i); and
  (iii): extracting betalains from the red beet plants harvested in step (ii) and thereby obtaining the betalain pigment composition.

Item 3. A method for obtaining a betalain pigment composition from red beet plants comprising the following steps:
  (i): foliar spraying red beet plants with an ethylene-generating compound;
  (ii): harvesting the red beet plants sprayed in step (i); and
  (iii): obtaining a juice comprising betalains from the red beet plants harvested in step (ii) and thereby obtaining the betalain pigment composition.

Item 4. The method according to any of the preceding items, wherein the ethylene-generating compound is selected from the group consisting of 2-chloroethylphosphonic acid; (2-chloroethyl)methylbis-(phenylmethoxy)silane; (2-chloroethyl)tris(2-methoxy-ethoxy)silane and/or 1-amino-cyclopropane-1-carboxylic acid.

Item 5. The method of item 4, wherein the ethylene-generating compound is 2-chloroethylphosphonic acid.

Item 6. The method of any of the preceding items, wherein the betalain pigment composition comprises betanin and vulgaxanthin.

Item 7. The method according to item 6, wherein the betanin to vulgaxanthin ratio is increased at least 5% compared to the control experiment without the use of ethylene-generating compound in step (i).

Item 8. The method according to item 6, wherein the betanin to vulgaxanthin ratio is increased at least 10% compared to the control experiment without the use of ethylene-generating compound in step (i).

Item 9. The method according to item 6, wherein the betanin to vulgaxanthin ratio is increased at least 15% compared to the control experiment without the use of ethylene-generating compound in step (i).

Item 10. The method according to item 6, wherein the betanin to vulgaxanthin ratio is increased at least 20% compared to the control experiment without the use of ethylene-generating compound in step (i).

Item 11. The method according to item 6, wherein the betanin to vulgaxanthin ratio is increased at least 25% compared to the control experiment without the use of ethylene-generating compound in step (i).

Item 12. The method according to any of the preceding items, wherein the isolating of betalains of step (iii) is done from at least 100 different harvested red beet plants.

Item 13. The method according to any of the preceding items, wherein the amount of obtained betalain pigments which are at least 5% higher (w/w) as compared to the amount of betalain pigments that are obtained in a control experiment without the use of ethylene-generating compound in step (i).

Item 14. The method according to any of the preceding items, wherein the amount of obtained betalain pigments which are at least 10% higher (w/w) as compared to the amount of betalain pigments that are obtained in a control experiment without the use of ethylene-generating compound in step (i).

Item 15. The method according to any of the preceding items, wherein the betalain to TSS (total soluble solids) ratio in the red beet is increased at least 5%, such as at least 10%, such as at least 15%, such as at least 20%, such as at least 25% compared to the control experiment without the use of ethylene-generating compound in step (i).

Item 16. The method according to any of the preceding items, wherein the amount of ethylene-generating compound applied at each spraying in step (i) of item 1 is an amount of from 20 g egc ha$^{-1}$ to 5000 g egc ha$^{-1}$.

Item 17. The method according to any of the preceding items, wherein the amount of ethylene-generating compound applied at each spraying in step (i) of item 1 is an amount of from 100 g egc ha$^{-1}$ to 1000 g egc ha$^{-1}$.

Item 18. The method according to any of the preceding items, wherein the total amount of ethylene-generating compound applied by spraying in step (i) on the red beet crop from sowing to harvest is an amount of more than 50 g egc ha$^{-1}$ to 10000 g egc ha$^{-1}$.

Item 19. The method according to any of the preceding items, wherein the total amount of ethylene-generating compound applied by spraying in step (i) on the red beet crop from sowing to harvest is an amount of more than 100 g egc ha$^{-1}$ to 5000 g egc ha$^{-1}$.

Item 20. The method according to any of the preceding items, wherein the foliar spraying of ethylene-generating compound of step (i) is done later than 2 weeks after planting.

Item 21. The method according to any of the preceding items, wherein the foliar spraying of ethylene-generating compound of step (i) is done at least 3 times before the harvesting the red beet plants of step (ii) and wherein harvesting of the red beet plants of step (ii) of item 1 is done later than 6 weeks after planting.

Item 22. A betalain pigment composition obtained by any of the preceding method items.

Item 23. The use of the betalain pigment composition of item 22 for coloring of an edible product.

Item 24. The use of item 23, wherein the product is an edible product and the edible product is a food product, a feed product, a pharmaceutical and/or a therapeutic product.

Item 25. The use of item 24, wherein the food product is selected from dairy product, juice, beverage, wine gum, marmalade, jam, confectionary, panned chocolate lentils, sausage casings, pasta, macaroni, cheese, prepared food and/or extruded foods The embodiments described herein can be further understood by reference to the following non-limiting examples.

EXAMPLES

Example 1

Foliar Spraying of Red Beet Plants with an Ethylene Generating Compound

Materials and Methods

Plants: Red beet Monty Rz and Belushi Rz. Seeds were provided by Rijk Zwaan (De Lier, Netherlands).

Etlylene generating compound (egc): 2-chloroethylphosphonic acid

Field trials were conducted at the Hoejbakkegaard (latitude 55, longitude 40.1-40.3; Denmark) in 2015, where three-row plots were arranged in randomized block designs with three replicates. Rainfall was complemented by irrigation throughout red beet growth to avoid water stress. Foliar applications of an ethylene generating compound (egc), 2-chloroethylphosphonic acid (CERONE® brand ETHEPHON, 39.9% active ingredient, Bayer Crop Science, Leverkusen, Germany), at a concentration of 360 g ha$^{-1}$ were performed with a $CO_2$ backpack spaced 50 cm apart, using manual spraying equipment designed for agricultural use. Egc application began 5 weeks after sowing and continued every 3 weeks, with a total of five applications. Plants were cultivated in loamy soil using techniques recommended for cultivation and plant protection in red beet crop production.

Trial 1. Plants were grown in plots consisted of 4.5 m-long rows, with a single harvest from the middle part of each row performed 16 weeks after sowing.

Trial 2. Plots consisted of 12 m-long rows, with several harvests from separate row segments performed during growth (3, 6, 9, 12, 15 and 18 weeks after sowing). For further analyses, biological replicates consisted of 20 whole beetroots harvested per plot.

Harvest and Sample Preparation

Biological replicates consisting of twenty beetroots were washed and split lengthwise. Of these, one pool of halves was ground and homogenized in a 3% sulfuric acid solution (1/1, w/w), using a Waring® two-speed commercial blender (VWR—Bie & Berntsen, Herlev, Denmark). The resulting fine homogenate was subsequently mixed with demineralized water (1/2, w/w) and vortexed. Finally, the sample was centrifuged for 20 min at 4500 rpm, and the supernatant (extract) was utilized for further analyses.

Determination of Betanin (Bn) and Vulgaxanthin (Vx) Content

Bn and Vx were measured spectrophotometrically. The beetroot extract was diluted to a proper concentration in 33 mM $KH_2PO_4$ (pH 6.5), and the absorption was measured at 476 nm and 538 nm for Bn and Vx, respectively, using a UV-visible spectrophotometer (Thermo Scientific Evolution™ 220, Waltham, Mass., USA). Bn and Vx concentrations were expressed in mg kg$^{-1}$ fresh weight (FW), using the corresponding absorbance, molecular weight and extinction coefficient for Bn and Vx.

Determination of Dry Matter (DM) and Total Soluble Solids Content (TSS)

TSS was measured with a manual refractometer (Refracto 30PX/GS Mettler-Toledo Inc., OH, USA) operating in the 0% to 85% Brix range. The beetroot extract was filtered through 0.45 µm membrane filters, and Brix measurements were performed using 1 mL of the filtrate.

DM was determined after samples were dried to a constant weight at 100° C. for 24 h, based on the difference in mass between the fresh and dry samples. TSS was then expressed as a percentage of the dry matter.

Results

Trial 1.

Effect of ethylene-generating compound treatment on betalain pigments and yield data of 16-week-old red beets.

The function of ethylene as a pre-harvest elicitor of betalain pigments was investigated in beetroots following foliar spray with egc. The effect of egc on Bn and Vx content was analyzed in the roots of 16-week-old plants. Overall, egc-treated plants exhibited increased Bn content in both cultivars studied. By contrast, Vx content did not vary significantly between untreated and treated plants. See Table 1 showing betanin (Bn) and vulgaxanthin (Vx) contents per FW and DW, betanin to vulgaxanthin ratio (Bn:Vx) and betalains to TSS ratio (Betalains:TSS) of egc-treated beetroot plants in trials harvested at a single time-point (16 weeks after sowing).

TABLE 1

| | Cultivar | egc (g ha$^{-1}$) | Betalains (mg kg$^{-1}$ FW) | | | | Betalains (g kg$^{-1}$ DM) |
| --- | --- | --- | --- | --- | --- | --- | --- |
| | | | Bn | Vx | Bn:Vx | Betalains:TSS | |
| Field trial 1 | Monty Rz | 0 | 1872 | 432 | 4.38 | 0.115 | 18.6 |
| | | 360 | 2166 | 386 | 5.79 | 0.154 | 21.9 |
| | Belushi Rz | 0 | 1240 | 339 | 3.67 | 0.090 | 13.9 |
| | | 360 | 1575 | 274 | 5.82 | 0.126 | 17.4 |
| Field trial 2 | Monty Rz | 0 | 1972 | 405 | 4.94 | 0.094 | 17.0 |
| | | 360 | 2458 | 364 | 6.88 | 0.132 | 21.5 |
| | Belushi Rz | 0 | 1418 | 276 | 5.28 | 0.074 | 12.9 |
| | | 360 | 1584 | 247 | 6.42 | 0.088 | 15.0 |

The mean root Bn content in treated plants of Monty Rz ranged from 2166 to 2458 mg kg$^{-1}$ FW, representing an increase of 25% compared with the values of untreated plants (1872 to 1972 mg kg$^{-1}$ FW). Similarly, Bn content in roots of treated plants of Belushi Rz displayed mean values of 1575 to 1584 mg kg$^{-1}$ FW, whereas the corresponding values in untreated plants ranged from 1240 to 1418 mg kg$^{-1}$ FW (Table 1), which represents an increase of 20% in average. As a result of increased Bn and unchanged Vx concentrations, the Bn:Vn increased substantially in both cultivars upon ethephon treatment (Table 1). Egc treated beetroots displayed lower DM than untreated roots. Consequently, differences in betalains (Bn+Vx) concentration per FW between untreated and treated roots were enhanced when data were expressed per DM (Table 1).

Egc treated beetroots of Monty Rz displayed mean Bn:Vx of 6.3, representing 34% increase compared with the ratio of untreated plants (4.7), whereas the corresponding ratio in Belushi Rz (6.1) represented 36% increase compared with the ratio of untreated plants (4.5). Ethephon applications had no significant effects on root FW for both cultivars or on beetroot yield in tons per hectare. Lowering soluble solids levels in the beet facilitate concentration of beetroot color during processing. Therefore, increasing betalains to TSS ratio (betalains:TSS) enhance the commercial value of the product. In the present work, egc treated beetroots displayed lower mean TSS and higher betalain content than untreated roots, which resulted in increased betalains:TSS in both cultivars (Table 1). This represents increases of 37% and 30% in average in Monty Rz and Belushi Rz, respectively.

Trial 2.

Betalain Accumulation During Root Growth.

The effect of 360 g egc ha−1 on Bn and Vx content DM and root size was followed during the whole growing period, 3, 6, 9, 12, 15 and 18 weeks after sowing, see table 2 showing betanin (Bn) and vulgaxanthin (Vx) contents, and betanin to vulgaxanthin ratio (Bn:Bx) monitored in roots of untreated and 360 g egc ha$^{-1}$ treated red beets (3-18 weeks after sowing). There were no significant differences in root mass and diameter between untreated and treated red beets of both cultivars at each harvest point.

Overall, compared with untreated plants, the mean root Bn was higher in roots of treated plants at every harvest point after treatments began and in average of all harvest Monty Rz showed 17% and Belushi Rz showed 10% higher Bn content. The opposite occurred with the mean root Vx, which displayed lower values in untreated plants during root growth, in average 5% less for Monty Rz and 20% less for Belushi Rz (Table 2). Differences in Bn concentration per FW between untreated and treated roots were enhanced when data were expressed per DM.

TABLE 2

| Weeks after sowing | egc (g ha$^{-1}$) | Monty Rz Betalains (mg kg$^{-1}$ FW) | | | Belushi Rz Betalains (mg kg$^{-1}$ FW) | | |
|---|---|---|---|---|---|---|---|
| | | Bn | Vx | Bn:Vx | Bn | Vx | Bn:Vx |
| 3 | 0 | 1562 | 39.4 | 39.7 | 987 | 33.0 | 30.0 |
| | 360 | 1343 | 32.3 | 41.6 | 945 | 24.3 | 39.0 |
| 6 | 0 | 2625 | 70.2 | 37.7 | 2465 | 70.2 | 40.5 |
| | 360 | 2867 | 62.3 | 46.5 | 2577 | 58.4 | 45.7 |
| 9 | 0 | 2495 | 154 | 16.2 | 1980 | 171 | 12.0 |
| | 360 | 2685 | 180 | 14.9 | 2144 | 128 | 17.2 |
| 12 | 0 | 1982 | 250 | 8.0 | 1551 | 208 | 7.52 |
| | 360 | 2475 | 239 | 10.5 | 1683 | 157 | 11.1 |
| 15 | 0 | 1766 | 383 | 4.62 | 1296 | 279 | 4.66 |
| | 360 | 2274 | 304 | 7.56 | 1442 | 211 | 6.84 |
| 18 | 0 | 1910 | 486 | 3.94 | 1180 | 306 | 3.87 |
| | 360 | 2219 | 455 | 4.89 | 1369 | 286 | 4.85 |

Bn and Vx content followed different kinetics during root growth. Bn content displayed a peak 9 weeks after sowing (2867 and 2577 mg kg$^{-1}$ FW in Monty Rz and Belushi Rz, respectively), followed by a gradual decrease until the end of the growing period (Table 2). In contrast, Vx content increased over time, reaching 486 and 306 mg kg$^{-1}$ FW in Monty Rz and Belushi Rz, respectively, at 18 weeks after sowing (Table 2). The highest Bn:Vx in both cultivars (46) was reached at early stages of root growth, 6 weeks after sowing, followed by a drop until the end of the growing period. The ratio Bn:Vx was in average over all harvests after 17% and 35% higher in the egc treated plants of Monty Rz and Belushi Rz, respectively.

The invention claimed is:

1. A method for obtaining a betalain pigment composition from red beet plants, comprising:
    (i) foliar spraying red beet plants with an ethylene-generating compound;
    (ii) harvesting the red beet plants sprayed in step (i); and
    (iii) isolating betalains from the red beet plants harvested in step (ii), thereby obtaining the betalain pigment composition.

2. The method according to claim 1, wherein the ethylene-generating compound is one or more selected from 2-chloroethylphosphonic acid; (2-chloroethyl)methylbis-(phenylmethoxy)silane; (2-chloroethyl)tris(2-methoxyethoxy)silane, and 1-amino-cyclopropane-1-carboxylic acid.

3. The method of claim 2, wherein the ethylene-generating compound is 2-chloroethylphosphonic acid.

4. The method of claim 1, wherein the betalain pigment composition comprises betanin and vulgaxanthin.

5. The method according to claim 4, wherein the betalain pigment composition has a betanin to vulgaxanthin ratio increased by at least 5% as compared to a betalain pigment composition obtained by a comparison method without the use of ethylene-generating compound in step (i).

6. The method according to claim 1, wherein step (ii) comprises isolating betalains of step (iii) from at least 100 different harvested red beet plants.

7. The method according claim 1, wherein the betalain pigment composition has a betalain pigment content at least 5% (w/w) higher as compared to a betalain pigment composition obtained by a comparison method without the use of ethylene-generating compound in step (i).

8. The method according to claim 1, wherein the betalain pigment composition has a betalain to total soluble solids (TSS) ratio is increased by at least 5% as compared to a betalain pigment composition obtained by a comparison method without the use of ethylene-generating compound in step (i).

9. The method according to claim 1, wherein the amount of ethylene-generating compound applied at each spraying in step (i) is from 20 g egc ha$^{-1}$ to 5000 g egc ha$^{-1}$.

10. The method according to claim 1, wherein the red beet plants are in a red beet crop and the total amount of ethylene-generating compound applied by spraying in step (i) on the red beet crop from sowing to harvest is from 50 g egc ha$^{-1}$ to 10000 g egc ha$^{-1}$.

11. The method according to claim 1, wherein the foliar spraying of ethylene-generating compound of step (i) is done later than 2 weeks after the red beet plants were planted.

12. The method according to claim 1, wherein the foliar spraying of ethylene-generating compound of step (i) is done at least 3 times before the harvesting the red beet plants of step (ii), wherein harvesting of the red beet plants of step (ii) is done later than 6 weeks after the red beet plants were planted.

* * * * *